(12) United States Patent
Jochinsen et al.

(10) Patent No.: US 10,779,721 B2
(45) Date of Patent: Sep. 22, 2020

(54) OPTICAL COHERENCE TOMOGRAPHY CROSS VIEW IMAGING

(71) Applicant: Alcon Inc., Fribourg (CH)

(72) Inventors: Mauricio Jochinsen, Fountain Valley, CA (US); Hugang Ren, Cypress, CA (US); Lingfeng Yu, Rancho Santa Margarita, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/717,171

(22) Filed: Sep. 27, 2017

(65) Prior Publication Data

US 2018/0104100 A1    Apr. 19, 2018

Related U.S. Application Data

(60) Provisional application No. 62/408,497, filed on Oct. 14, 2016.

(51) Int. Cl.
| | | |
|---|---|---|
| *A61B 3/00* | (2006.01) | |
| *G01B 9/02* | (2006.01) | |
| *A61B 3/10* | (2006.01) | |
| *G06T 3/00* | (2006.01) | |
| *A61F 9/008* | (2006.01) | |

(52) U.S. Cl.
CPC ............ *A61B 3/0025* (2013.01); *A61B 3/102* (2013.01); *G01B 9/02091* (2013.01); *G06T 3/0006* (2013.01); *A61F 2009/00851* (2013.01); *A61F 2009/00897* (2013.01); *G06T 2207/10101* (2013.01); *G06T 2207/20212* (2013.01); *G06T 2207/20221* (2013.01); *G06T 2207/30041* (2013.01)

(58) Field of Classification Search
CPC .. A61B 3/0025; A61B 3/102; G01B 9/02091; G06T 3/0006; G06T 2207/10101; G06T 2207/30041; G06T 2207/20221; G06T 2207/20212; A61F 2009/00851; A61F 2009/00897
See application file for complete search history.

(56) References Cited

U.S. PATENT DOCUMENTS

| | | | |
|---|---|---|---|
| 2008/0204655 A1* | 8/2008 | Kikawa | A61B 3/102 351/206 |
| 2008/0309881 A1 | 12/2008 | Huang et al. | |
| 2009/0103049 A1 | 4/2009 | McLean et al. | |
| 2010/0027857 A1* | 2/2010 | Wang | A61B 3/102 382/128 |
| 2010/0142780 A1 | 6/2010 | Yasuno et al. | |
| 2010/0165289 A1 | 7/2010 | Nozato et al. | |
| 2011/0007957 A1 | 1/2011 | Sakagawa | |

(Continued)

FOREIGN PATENT DOCUMENTS

| | | | | |
|---|---|---|---|---|
| WO | WO-2016110917 A1 * | 7/2016 | ......... | G01B 9/02027 |
| WO | 2016/133762 A1 | 8/2016 | | |

OTHER PUBLICATIONS

James Strong; "Retinal OCT Imaging"; Penn State Hershey Eye Center, Hershey, Pennsylvania; Website: OCT Imaging; https://www.opsweb.org/?page=RetinalOCT (Copyright © 2011-2017 The Author(S) and The Ophthalmic Photographers' Society Inc.).

*Primary Examiner* — Michael P LaPage

(57) ABSTRACT

An optical coherence tomography (OCT) system and method for cross view imaging using at least two B-scan images transformed and coupled to each other at an angle to generate a cross view image.

29 Claims, 4 Drawing Sheets

(56) References Cited

U.S. PATENT DOCUMENTS

| | | | |
|---|---|---|---|
| 2011/0141259 A1* | 6/2011 | Nakano | A61B 3/0025 348/78 |
| 2011/0299034 A1* | 12/2011 | Walsh | A61B 3/102 351/206 |
| 2012/0070049 A1* | 3/2012 | Iwase | G06T 7/0012 382/128 |
| 2012/0321166 A1* | 12/2012 | Kitamura | A61B 3/0058 382/131 |
| 2013/0002711 A1* | 1/2013 | Sakagawa | A61B 3/0025 345/619 |
| 2014/0029826 A1* | 1/2014 | Pintal | G06T 11/008 382/131 |
| 2014/0200853 A1* | 7/2014 | Guan | G01N 29/069 702/189 |
| 2014/0218686 A1* | 8/2014 | Reisman | G06T 7/0012 351/206 |
| 2015/0042949 A1 | 2/2015 | Jeglorz et al. | |
| 2016/0066778 A1* | 3/2016 | Imamura | A61B 3/0091 351/206 |
| 2016/0296376 A1* | 10/2016 | Rill | A61F 9/00825 |
| 2017/0000327 A1* | 1/2017 | Fingler | A61B 3/0025 |
| 2018/0014725 A1* | 1/2018 | Bagherinia | A61B 3/0025 |

* cited by examiner

OPTICAL COHERENCE TOMOGRAPHY CROSS VIEW IMAGING

BACKGROUND

Field of the Disclosure

This disclosure relates to optical coherence tomography (OCT) and more particularly to systems and methods for OCT cross view imaging.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. During ophthalmic surgery, an ophthalmologist might use an imaging technology, such as an optical coherence tomography (OCT) system, to attain medical diagnostic information relating to various eye diseases and disorders.

OCT is an interferometry analysis technique, which analyzes the time delay and magnitude changes of low coherence light as it is backscattered by biological sample tissues. In an OCT system, a low coherence light beam is split into a sample arm, which moves in the direction of a sample, and a reference arm, which moves in the direction of a reference mirror. As the sample arm and reference arm are reflected back to the OCT system, they are combined to create an interference pattern that may be used to measure distances and depth profiles of the sample. In ophthalmic surgery for example, an OCT system may be used to provide cross sectional views of a retina in high resolution.

SUMMARY

In one aspect, the invention relates to an optical coherence tomography (OCT) system containing a processor coupled to a computer readable medium. The OCT system also contains computer-executable instructions carried on the computer readable medium, the instructions readable by the processor, the instructions, when read and executed, for causing the processor to acquire a first B-scan image and a second B-scan image; transform each B-scan image; and couple the first B-scan post-transformation image to the second B-scan post-transformation image at an angle to generate a cross view image.

Another disclosed aspect relates to a machine readable storage medium, comprising computer-executable instructions carried on the computer readable medium, the instructions readable by a processor, the instructions, when read and executed, for causing the processor to acquire a first B-scan image and a second B-scan image; transform each B-scan image; and couple the first B-scan post-transformation image to the second B-scan post-transformation image at an angle to generate a cross view image.

Another disclosed aspect relates to a method for cross view imaging using an optical coherence tomography system (OCT), the method comprising acquiring a first B-scan image and a second B-scan image; transforming each B-scan image; and coupling the first B-scan post-transformation image to the second B-scan post-transformation image at an angle to generate a cross view image.

The above systems, machine readable storage medium, and method may be combined with one another. In addition, they may be combined with one or more of the following additional aspects, unless clearly mutually exclusive: i) the first B-scan image may correspond to a first B-scan and the second B-scan image may corresponds to a second B-scan; ii) the first B-scan may be coupled to the second B-scan; iii) the coupling point of the first B-scan post-transformation image to the second B-scan post transformation image may approximately match the coupling point of the first B-scan to the second B-scan; iv) the angle between the first B-scan post-transformation image and the second B-scan post-transformation image may range between 30 degrees and 170 degrees; v) the first B-scan post-transformation image and the second B-scan post-transformation image may be coupled at either end of each image; vi) the first B-scan post-transformation image and the second B-scan post-transformation image may be coupled at any point along each image; vii) the transformation may be a perspective transformation; viii) the cross view image may further include a third B-scan image and a fourth B-scan image; ix) the system may further include a display; x) the cross view image may be presented on the display; xi) the cross view image may be presented on the display with no more than a 120 millisecond delay from when the first B-scan is acquired; xii) the cross view image may be presented on the display with no more than a 1 second delay from when the first B-scan is acquired; xiii) a three-dimensional raster scan data set may be presented on the display when one of the B-scan post-transformation images is moving in a manner controlled by a user; xiv) the cross view image may be presented on the display simultaneously with one or more B-scans.

BRIEF DESCRIPTION OF THE DRAWINGS

For a more complete understanding of the present invention and its features and advantages, reference is now made to the following description, taken in conjunction with the accompanying drawings, which are not drawn to scale, and in which.

DETAILED DESCRIPTION

Figure 1:
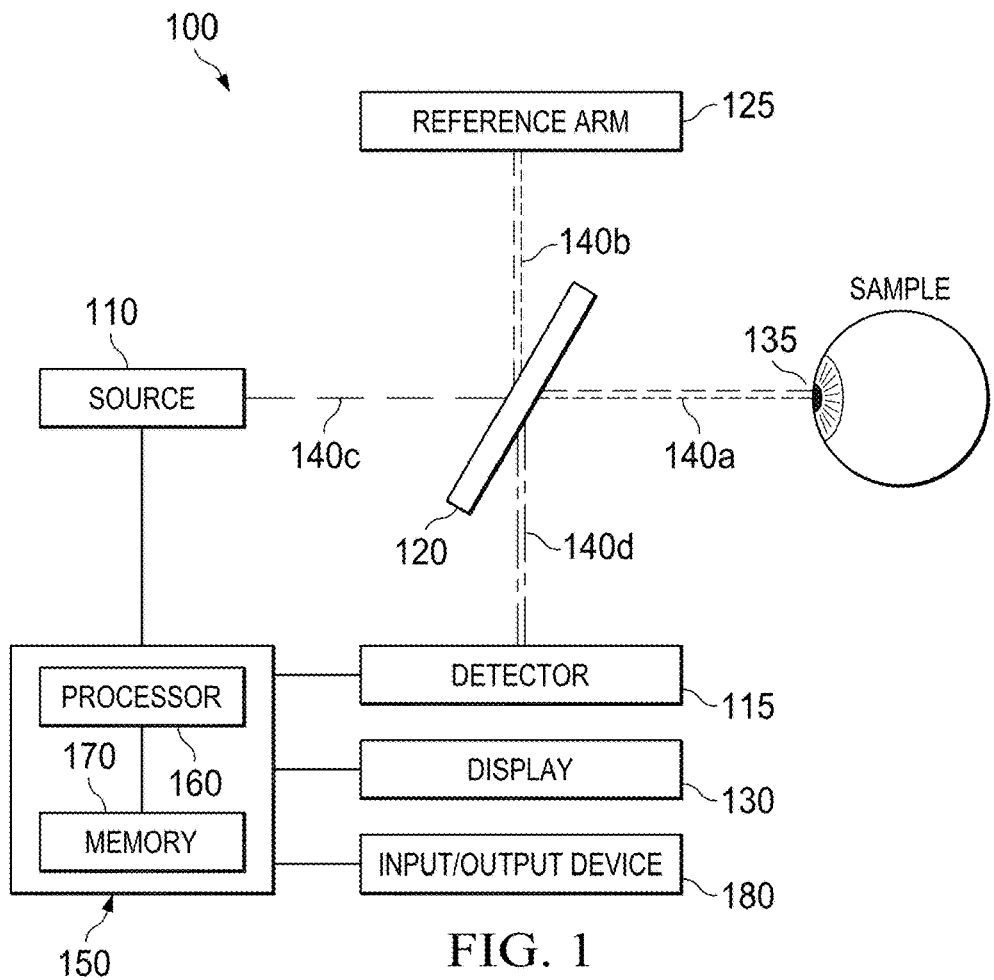
FIG. 1 is a schematic diagram of an OCT system with cross view imaging.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a reference numeral followed by a letter refers to a specific instance of an element and the numeral only form of the reference numeral refers to the collective element. Thus, for example, device '12a' refers to an instance of a device class, which may be referred to collectively as devices '12' and any one of which may be referred to generically as a device '12'.

OCT is an interferometric analysis technique for structural examination of a sample, such as a tissue that is at least partially reflective to light. It can also be used for functional examination of a sample, such as the motion and velocity of the sample or blood flow in a tissue. In OCT, an OCT beam is split into a reference beam and a sample beam and then recombined. The recombined OCT beam is used to measure distances and depth profiles based on optical interference that arises between the reference beam and the sample beam because the sample beam interacts with the sample, such as a biological tissue. The OCT beam may be supplied in pulses, sweeping wavelengths, or a broad band light.

An OCT system may be used during surgery to create an image, such as a cross view image. A cross view image is created using cross view imaging. A cross view image is composed of at least two B-scan images transformed and coupled to each other at an angle, as discussed below in more detail.

Referring now to the figures, FIG. 1 is schematic diagram of an OCT system 100 that may be used with cross view imaging.

OCT system 100 may include a display device (not shown), such as a two-dimensional image display, a monitor, a TV, or any other suitable device for presenting images, including OCT images, video, and alphanumeric characters recognizable to a user. OCT system 100 may display a two-dimensional (2D) image or a three-dimensional (3D) image using the display device. In surgery, OCT system 100 may present the surgeon with an OCT image in sufficient time to use the image to modify the surgery while it is occurring. For instance, and as discussed below in more detail in reference to FIGS. 2-5, the image may include a cross view image presented with no more than a 1 second delay from when the first B-scan is acquired. For example, the cross view image may be presented with no more than a 120 millisecond (ms) delay from when the first B-scan is acquired.

OCT system 100 additionally includes OCT source 110 and OCT transmission medium 140, which may be an optical fiber. OCT source 110 produces an OCT beam (not shown) that travels through OCT transmission medium 140c to beam splitter 120 where it is split so that a portion of the beam called the sample beam travels through OCT transmission medium 140a to a beam scanning unit (not shown), which scans sample 135, such as an eye tissue. A separate portion of the OCT beam called the reference beam travels through OCT transmission medium 140b to reference arm 125. Reference arm 125 may include a mirror to reflect the reference beam.

After hitting reference arm 125 or tissue 135, the reference or sample beams travel back through OCT transmission mediums 140b and 140a, respectively, to beam splitter 120, where the sample beam interferes with the reference beam to generate a recombined OCT beam, which may have an interference pattern. This recombined OCT beam is directed via OCT transmission medium 140d to detector 115. Detector 115 may be a spectrometer. Alternatively, detector 115 may include a photodiode or similar device that generates an electrical signal indicative of incident light intensity at detector 115. Detector 115 sends a signal, which may be electrical or wireless, to computer 150. The signal reflects a property of the recombined OCT beam.

Computer 150 may include circuitry for signal conditioning, demodulation, digitization, and digital signal processing. Computer 150 also includes an image coupling module (not shown) for coupling two or more images together and an image transformation module (not shown) for applying a perspective transformation to an image, as discussed in more detail in reference to FIG. 2. These modules may be implemented as separate software or hardware modules, or combined into a single module, such as software implemented on processor 160. Additionally, computer 150 may provide OCT images, OCT data, or both to a remotely located computer (not shown), which includes an image coupling module and image transformation module.

Computer 150 also includes memory media 170, input/output device 180, and processor 160. Memory media 170 may include non-transitory computer-readable media that stores data and instructions, such as executable code, for at least a period of time. The instructions are executable by processor 160 having access to memory media 170. Memory media 170 may include persistent and volatile media, fixed and removable media, and magnetic and semiconductor media. Memory media 170 may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and various combinations of the foregoing.

Input/output device 180 may be communicatively coupled to processor 160 and may include any instrumentality or instrumentalities, which allow a user to interact with computer 150 and its associated components by facilitating input from a user and output to a user. Facilitating input from a user allows the user to manipulate computer 150 and facilitating output to a user allows computer 150 to indicate effects of the user's manipulation. For example, input/output device 180 may allow a user to input data, instructions, or both into computer 150, and otherwise manipulate computer 150 and its associated components. Input/output devices may include user interface devices, such as a keyboard, a mouse, a touch screen, a joystick, a handheld lens, a tool tracking device, a coordinate input device, or any other I/O device suitable to be used with an OCT system.

Processor 160 may include any suitable system, device, or apparatus operable to interpret and execute program instructions, process data, or both stored in memory 170. Processor 160 further may include one or more microprocessors, microcontrollers, digital signal processors (DSPs), application specific integrated circuits (ASICs), or other circuitry configured to interpret and execute program instructions, process data, or both. Processor 160 processes information received in the signal from detector 115 about any interference pattern in the recombined OCT beam, to create a mathematical representation of tissue 135. The mathematical representation may then be used to create an electronic OCT image of the tissue.

The electronic OCT image of the tissue is presented on a display device 130 in any of a variety of images, such as in a one-dimensional (1D) image, such as an A-scan image, a 2D image, such as a B-scan image, a 3D volume, or a cross view image, as will be described in further detail below in reference to FIGS. 2-5.

An A-scan image is a 1D image of the OCT light scattering profile of tissue 135 as a function of depth into the tissue roughly parallel to the sample beam. A-scan images can be used to generate a B-scan image and a 3D volume data set. A B-scan image is a 2D cross-sectional image of tissue 135 obtained by laterally combining a series of A-scan images. Alternatively, a B-scan image can be obtained from a 3D volume data set.

Each B-scan image corresponds to a B-scan. A B-scan is a cross-sectional scan. Depending on the clinical application of a B-scan image, each B-scan across a cross-section of tissue 135 may have the same or a different size, length, width, and shape. For example, a first B-scan of a tissue may be 1 millimeter (mm) long, and another B-scan of the same tissue may be 16 mm long. B-scans may be arranged in any pattern. For example, B-scans may be arranged parallel to each other, they may be arranged in a radius from a common crossing point to create the image of a circular area, or they may be arranged as a raster scan. A collection of consecutive B-scans can be used to construct a 3D volume image. However, 3D volume images are opaque so only the most outer surface of the 3D volume image can be analyzed or read. Structures inside the 3D volume image cannot be analyzed or read. Cross view imaging allows some 3D information to be gained from B-scans without many of the problems (e.g., large data, processing time, opaque surfaces, and selection of desired location/planes) associated with 3D volume images.

Figure 2:
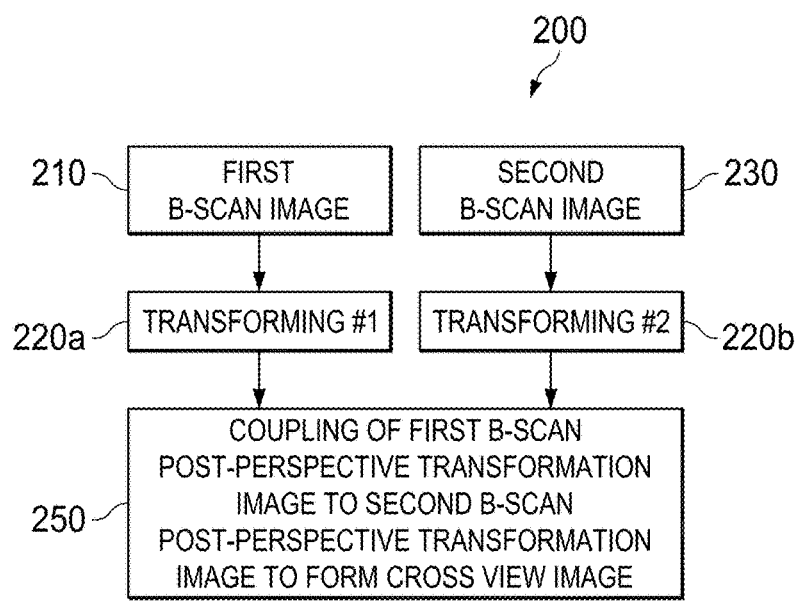
FIG. 2 is a flow chart of a method of cross view imaging.

FIG. 2 is a flowchart for cross view imaging using OCT, such as OCT system 100. Although FIG. 2 discloses a particular number of steps to be taken with respect to method 200, method 200 may be executed with greater or lesser steps than those depicted in FIG. 2. Additionally, although FIG. 2 discloses a certain order of steps to be taken with respect to method 200, the steps of method 200 may be completed simultaneously, near simultaneously, or in any suitable order, so long as method 200 is completed and cross view image is presented on a display. Depending on the circumstances, a cross view image may be presented on a display within a certain time frame. For example, during surgery, the cross view image may be presented on a display within 121 ms or 1 second from when the first B-scan is acquired.

At step 210, one B-scan image is acquired by the OCT system. Similarly, at step 230, a second B-scan image is acquired by the OCT system. The first B-scan image corresponds to a first B-scan, and the second B-scan image corresponds to a second B-scan. The first and second B-scans may be coupled at each end of each B-scan or may be coupled at any point along each B-scan and in any manner (e.g., intersecting B-scans), At steps 220*a* and 220*b*, a perspective transformation is performed on each B-scan image. A perspective transformation may be carried out through any suitable mathematical model known in the art, such as an affine transformation.

Figure 3A:
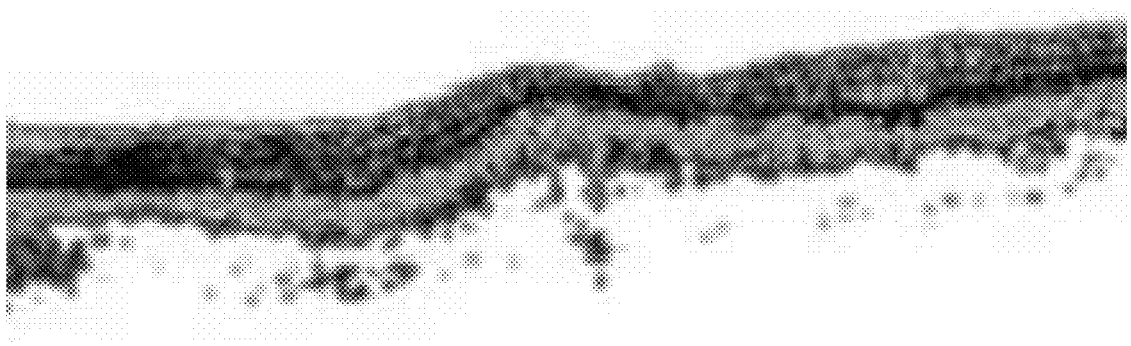
FIG. 3A is a conventional OCT B-scan image.
Figure 3B:
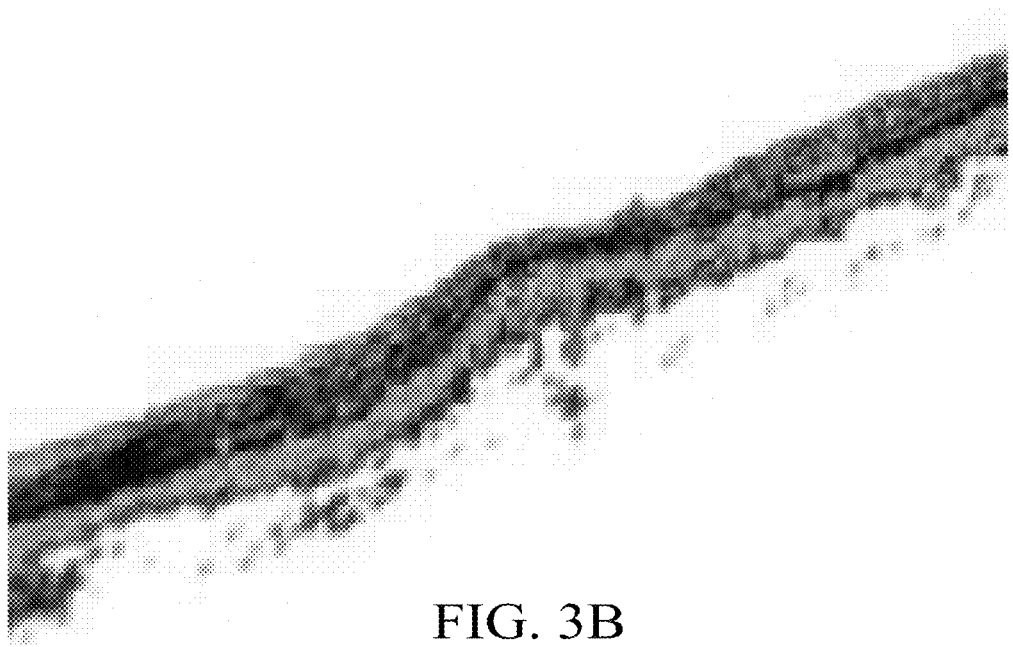
FIG. 3B is an OCT B-scan image of FIG. 3A after a perspective transformation.

FIG. 3 shows a B-scan image before and after a perspective transformation is applied. More specifically, FIG. 3A shows a conventional B-scan image. FIG. 3B shows the B-scan image of FIG. 3A but with a perspective transformation applied.

Figure 4:
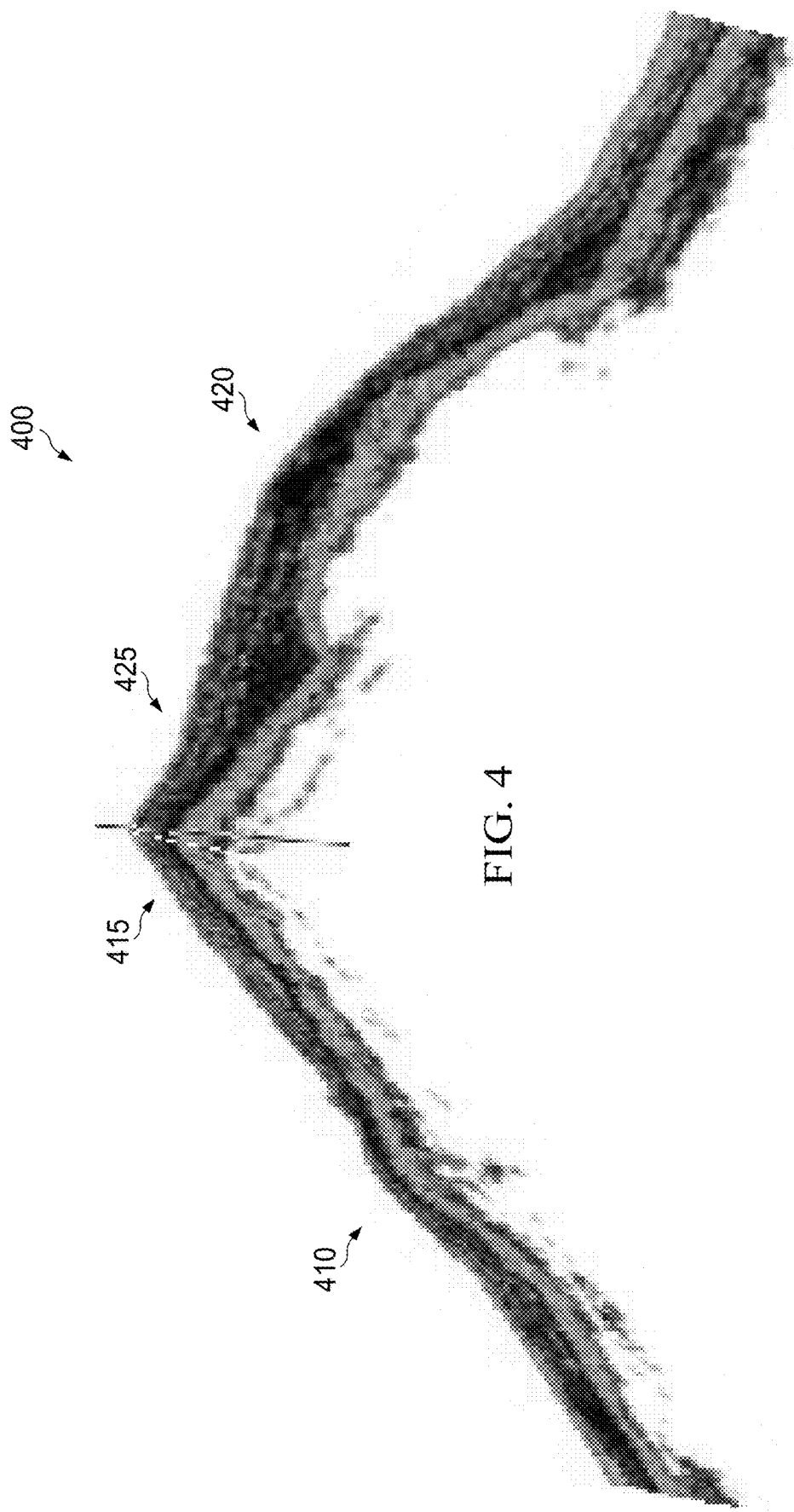
FIG. 4 is an OCT image created using cross view imaging.
Figure 5:
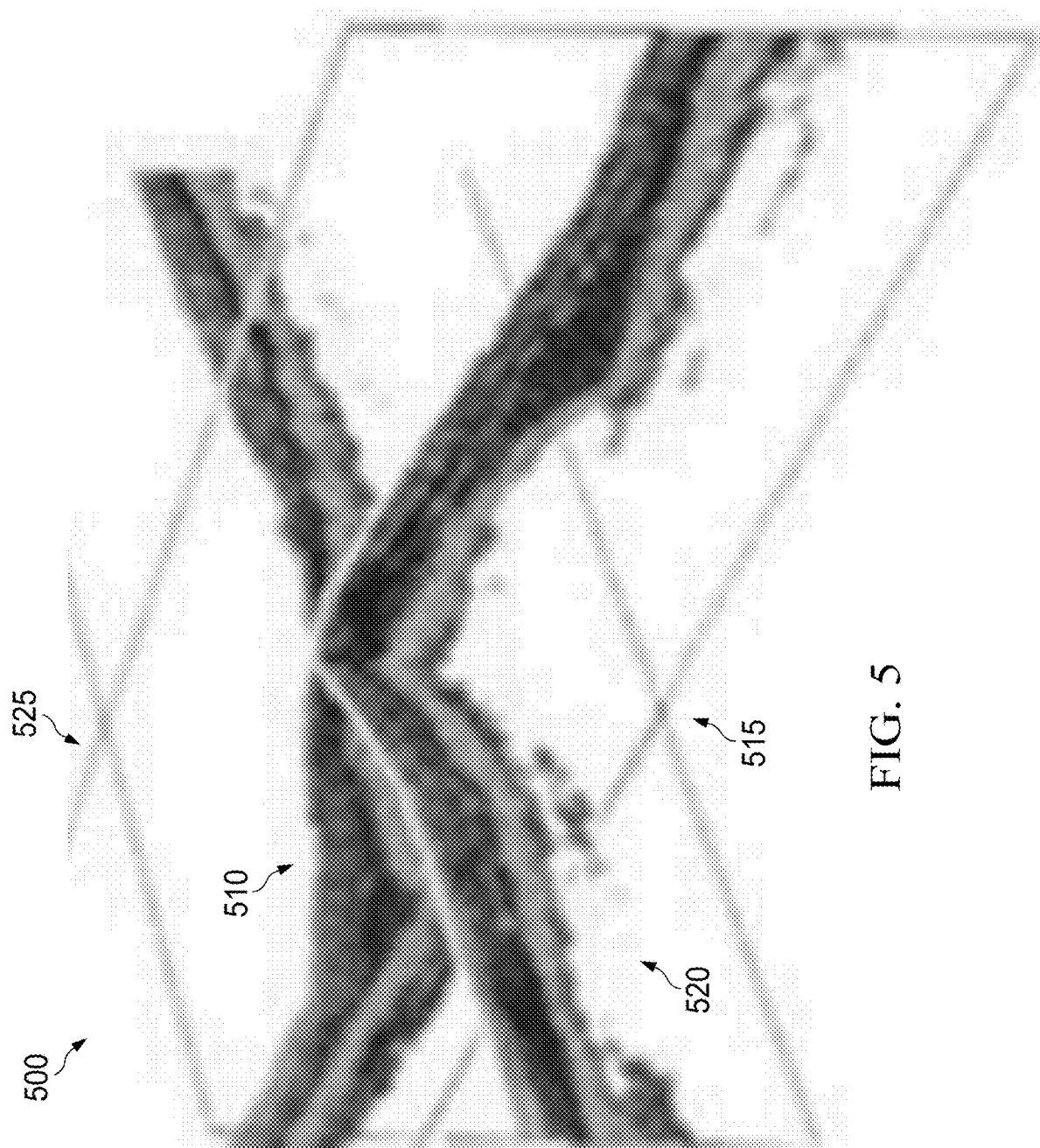
FIG. 5 is an OCT center crossed image created using cross view imaging.

At step 250, the first B-scan post-perspective transformation image and the second B-scan post-perspective transformation image are coupled via cross view imaging at an angle to generate a cross view image. The angle may range between 30 degrees and 170 degrees. The first B-scan post-perspective transformation image and the second B-scan post-perspective transformation image are coupled such that they approximately match the coupling of the corresponding B-scans. The two B-scan post-perspective transformation images may be coupled at each end of each B-scan post-perspective transformation image if their corresponding B-scans are coupled at each end of each B-scan. For example, and as shown in FIG. 4, B-scan post-perspective transformation image 410 may be coupled to B-scan post-perspective transformation image 420 at end 415 of B-scan post-perspective transformation image 410 and at end 425 of B-scan post-perspective transformation image 420. Alternatively, B-scan post-perspective transformation image 410 and B-scan post-perspective transformation image 420 may be coupled at any point along each B-scan post-perspective transformation image and in any manner (e.g., intersecting images), so long as cross view image 400 is readable by a user and so long as the coupling matches approximately the coupling of the corresponding B-scans. For example, if the corresponding B-scans are coupled at the center of each B-scan such that the B-scans intersect at each B-scan's center, then the two B-scan post-perspective transformation images may be coupled to approximately match the coupling of the corresponding B-scans. Thus, as shown in FIG. 5, the two B-scan post-perspective transformation images may be coupled at the center of each B-scan post-perspective transformation image such that each B-scan post-perspective transformation image intersects the other at each B-scan post-perspective transformation image's center. In FIG. 5, B-scan post-perspective transformation image 510 is coupled to B-scan post-perspective transformation image 520 at center 525 of B-scan post-perspective transformation image 510 and at center 515 of B-scan post-perspective transformation image 520.

Following the method of FIG. 2, the cross view image may be presented on a display device alone or simultaneously with one or more B-scans. For instance, cross view image 400, as described above in reference to FIG. 4, and cross view image 500, as described above in reference to FIG. 5, may be presented on a display alone or simultaneously with one or more B-scans.

Additionally, based on the cross view image, a 3D raster scan data set can be displayed to a user when only one of the B-scan post-perspective transformation images is moving through the 3D volume data in a manner controlled by the user. For example, after two B-scan post-perspective transformation images are coupled, one of the B-scan post perspective transformation images may be fixed or moving in a fixed position. The other B-scan post perspective transformation image may be controlled by the user such that the user can move the B-scan post perspective transformation image in any direction.

Although FIG. 2 illustrates a method using two B-scan images, any number more than two may be used by applying a similar methodology. For example, a third B-scan post-perspective transformation image and a fourth B-scan post-perspective transformation image may be coupled to the first B-scan post-perspective transformation image and the second B-scan post-perspective transformation image at any point along each image and in any manner, so long as the cross view image is readable by a user. Further, although FIG. 2 illustrates a method for using B-scan images, 2D B-scan images may be extracted from a 3D volume scan to generate a cross view image.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. An optical coherence tomography (OCT) system comprising:
   a processor coupled to a non-transitory computer readable medium; and
   computer-executable instructions carried on the non-transitory computer readable medium, the instructions readable by the processor are executed to cause the processor to:
   acquire a first B-scan image and a second B-scan image;
   perform a perspective transformation on each B-scan image;
   couple the first B-scan post-transformation image to the second B-scan post-transformation image at an angle of between 30 degrees and 170 degrees to generate a cross view image; and
   display the cross view image by displaying the first B-scan post-transformation image and the second B-scan post-transformation image as two B-scan cross-section views of a three dimensional volume, wherein the first b-scan post-transformation image displayed is arranged at an angle of between 30 degrees and 170 degrees with respect to the second b-scan post-transformation image displayed, and the first b-scan post-transformation image is displayed simultaneously with the second b-scan post-transformation image.

2. The OCT system of claim 1, wherein the first B-scan image corresponds to a first B-scan and the second B-scan image corresponds to a second B-scan.

3. The OCT system of claim 2, wherein the first B-scan is coupled to the second B-scan.

4. The OCT system of claim 3, wherein the coupling point of the first B-scan post-transformation image to the second B-scan post transformation image approximately matches the coupling point of the first B-scan to the second B-scan.

5. The OCT system of claim 1, wherein the first B-scan post-transformation image and the second B-scan post-transformation image are coupled at either end of each image.

6. The OCT system of claim 1, wherein the first B-scan post-transformation image and the second B-scan post-transformation image are coupled at any point along each image.

7. The OCT system of claim 1, wherein the transformation is a perspective transformation.

8. The OCT system of claim 7, wherein a three-dimensional raster scan data set is presented on the display when one of the B-scan post-transformation images is moving in a manner controlled by a user.

9. The OCT system of claim 7, wherein the cross view image is presented on the display simultaneously with one or more B-scans.

10. The OCT system of claim 1, wherein the cross view image further comprises a third B-scan image and a fourth B-scan image.

11. The OCT system of claim 1, further comprising a display.

12. The OCT system of claim 11, wherein the cross view image is presented on the display.

13. The OCT system of claim 12, wherein the cross view image is presented on the display with no more than a 120 millisecond delay from when the first B-scan is acquired.

14. The OCT system of claim 12, wherein the cross view image is presented on the display with no more than a 1 second delay from when the first B-scan is acquired.

15. The system of claim 1 wherein an affine transformation is used to perform a perspective transformation on each B-scan image.

16. A method for cross view imaging using an optical coherence tomography system (OCT), the method comprising:
   acquiring a first B-scan image and a second B-scan image;
   performing a perspective transformation on each B-scan image;
   coupling the first B-scan post-transformation image to the second B-scan post-transformation image at an angle of between 30 degrees and 170 degrees to generate a cross view image; and
   displaying the cross view image by displaying the first B-scan post-transformation image and the second B-scan post-transformation image as two B-scan cross-section views of a three dimensional volume, wherein the first b-scan post-transformation image displayed is arranged at an angle of between 30 degrees and 170 degrees with respect to the second b-scan post-transformation image displayed, and the first b-scan post-transformation image is displayed simultaneously with the second b-scan post-transformation image.

17. The method of claim 16, wherein the first B-scan image corresponds to a first B-scan and the second B-scan image corresponds to a second B-scan.

18. The method of claim 17, further comprising coupling the first B-scan to the second B-scan.

19. The method of claim 17, wherein the coupling point of the first B-scan post-transformation image to the second B-scan post transformation image approximately matches the coupling point of the first B-scan to the second B-scan.

20. The method of claim 16, further comprising coupling the first B-scan image and the second B-scan image at either end of each B-scan image.

21. The method of claim 16, further comprising coupling the first B-scan image and the second B-scan image at any point along each image.

22. The method of claim 16, further comprising transforming each B-scan image by applying a perspective transformation.

23. The method of claim 16, further comprising acquiring a third B-scan image and a fourth B-scan image and coupling each to the first B-scan image and the second B-scan image.

24. The method of claim 16, further comprising presenting the cross view image on a display.

25. The method of claim 24, further comprising presenting the cross view image on the display with no more than a 120 millisecond delay from when the first B-scan is acquired.

26. The method of claim 24, further comprising presenting the cross view image on the display with no more than a 1 second delay from when the first B-scan is acquired.

27. The method of claim 24, further comprising presenting a three-dimensional raster scan data set on the display when one of the B-scan post-transformation images is moving in a manner controlled by a user.

28. The method of claim 24, further comprising simultaneously presenting the cross view image with one or more B-scans on the display.

29. The method of claim 16 wherein performing a perspective transformation on each B-scan image further comprises performing an affine transformation on each B-scan image.

* * * * *